United States Patent [19]

Lantz et al.

[11] Patent Number: 5,386,068
[45] Date of Patent: Jan. 31, 1995

[54] STABILIZATION OF 1,1-DICHLORO-1-FLUOROETHANE

[75] Inventors: Andre Lantz, Vernaison; Rene Bertocchio, Vourles par Vernaison; Patrick Lambert, Caluire, all of France

[73] Assignee: d'Elf Atochem S.A., France

[21] Appl. No.: 957,841

[22] Filed: Oct. 8, 1992

[30] Foreign Application Priority Data

Oct. 11, 1991 [FR] France .................. 91 12542

[51] Int. Cl.⁶ .................. C07C 17/42; C07C 19/02
[52] U.S. Cl. .................... 570/122; 570/121
[58] Field of Search ................ 570/122, 121

[56] References Cited

U.S. PATENT DOCUMENTS

| | | | |
|---|---|---|---|
| 3,090,818 | 5/1963 | Long | 260/652.5 |
| 3,627,834 | 12/1971 | Patron | 260/652.5 R |
| 5,120,461 | 6/1992 | Logsdon et al. | 570/122 |
| 5,169,995 | 12/1992 | Crooker et al. | 570/122 |

FOREIGN PATENT DOCUMENTS

| | | |
|---|---|---|
| 3434886 | 3/1986 | Germany . |
| 5422 | 1/1981 | Japan ................ 570/122 |
| 1018809 | 2/1966 | United Kingdom . |

OTHER PUBLICATIONS

Chemical Abstracts, vol. 111, No. 19, Nov. 6, 1989, Appln. No. 53-78075, "Stabilization of Lower Aliphatic Chloro-Fluorohydrocarbon".
Patent Abstracts of Japan, vol. 3, No. 79, Appln. No. 52-118601, "Stabilization of Flon".
Patent Abstracts of Japan, vol. 5, No. 54, Appln. No. 54-79100, "Stabilization of Chlorinated and Fluorinated Lower Aliphatic Hydrocarbon".
Patent Abstracts of Japan, vol. 4, No. 30, Appln. No. 53-78074, "Stabilization of Lower Aliphatic Chloro-Fluoro Hydrocarbon".
European Search Report, Republique Francaise, FR 9112542, FA 462203.

Primary Examiner—Joseph E. Evans
Attorney, Agent, or Firm—Morgan & Finnegan

[57] ABSTRACT

In order to stabilize 1,1-dichloro-1-fluoroethane containing traces of vinylidene chloride, at least one ethylenic hydrocarbon containing at least 4 carbon atoms is added thereto.

9 Claims, No Drawings 5,386,068

STABILIZATION OF 1,1-DICHLORO-1-FLUOROETHANE

FIELD OF THE INVENTION

The present invention relates to the stabilization of 1,1-dichloro-1-fluoroethane. This compound, also called HFA 141b, has been proposed as a substitute for chlorofluorocarbons (CFCs), in particular in the field of blowing agents for polymer foams, for example as a substitute for trichlorofluoromethane (CFC 11), and in the field of solvents as a substitute for 1,1,2-trichloro-1,2,2-trifluoroethane (CFC 113).

BACKGROUND OF THE INVENTION

HFA 141b can be prepared by reacting vinylidene chloride (also designated by $CV_2$) or 1,1,1-trichloroethane with hydrofluoric acid. These processes can be carried out either in the gaseous phase or in the liquid phase, and in the absence or in the presence of catalysts. Numerous patents relating to these manufacturing processes have been published (U.S. Pat. No. 2,894,044, EP 391,102 and EP 353,059 for gaseous phase fluorination; U.S. Pat. No. 3,833,676 for liquid phase fluorination without a catalyst; EP 361,578, EP 378,942 and EP 391,103 for liquid phase fluorination in the presence of a catalyst).

All these processes nevertheless supply an HFA 141b containing small quantities of $CV_2$. This $CV_2$ can be the result of incomplete conversion in the case of the $CV_2$+HF process, but in the case of the 1,1,1-trichloroethane+HF process it can also be the result of decomposition of the trichloroethane. In both of the two processes, $CV_2$ can also be formed by decomposition of HFA 141b, in particular during the final treatments such as, for example, distilling, purifying and drying. Vinylidene chloride can also be present in HFA 141b in concentrations of the order of 200 ppm to 1%.

Other ethylenic impurities can also be present in HFA 141b, such as 1,1-chlorofluoroethylene, but in a much lower quantity.

$CV_2$ and other ethylenic impurities are undesirable in large quantities in the use of HFA 141b and the specifications in regard to $CV_2$ or in regard to the mixture $CCl_2=CH_2+CFCl=CH_2$ have been fixed at a value less than 500 ppm.

Various processes have been proposed for carrying out the elimination of $CV_2$ in HFA 141b. Thus, U.S. Pat. Nos. 4,940,824 and 4,950,816 describe selective absorption of $CV_2$ on carbon-based molecular sieves and on activated charcoals; however, the absorption capacities of the two absorbents are not very large and it is difficult to be able to go down economically to a content much less than 200 ppm.

Other purifying processes have also been described, such as eliminating ethylenic impurities by photochlorination and/or by reacting with a hydracid (EP 401,493, EP 420,709 and U.S. Pat. No. 4,962,244). Although these processes are very efficient, it is difficult entirely to eliminate all traces of these ethylenic impurities (in particular of $CV_2$), and it would be advantageous to be able to market an HFA 141b which still contains a few hundred ppm of $CV_2$ but is nevertheless stable.

Pure HFA 141b is a perfectly stable product which undergoes no conversion or decomposition. Conversely, in the presence of certain compounds such as for example alcohols, HFA 141b can decompose; the U.S. Pat. No. 4,816,174 thus describes stabilization by nitromethane of HFA 141b/methanol mixtures. In the presence of alcohols or polyols, most chlorofluorocarbons or chlorofluorohydrocarbons also have to be stabilized, and numerous stabilizers have thus been proposed, such as epoxybutene (JP 01056630), α-methylstyrene (JP 01050829), acrylic or methacrylic esters (JP 01211538), nitromethane (JP 01128944), mixtures of nitrated derivatives and epoxides (JP 01128945), mixtures of derivatives of styrene and epoxides, phenols, acrylic or methacrylic esters (JP 01056631, JP 01056632 and JP 01211539).

The aforementioned patents in fact only relate to stabilization of chlorofluorocarbons and chlorofluorohydrocarbons during their use, most particularly during their use as blowing agents for plastic foams. To our knowledge there exists no document relating to stabilization of HFA 141b itself.

The applicant has found that an HFA 141b containing $CV_2$ evolves slowly during storage. This instability is exhibited even for HFA 141b containing only small quantities of $CV_2$, that is to say approximately 100 to 500 ppm or even less. The evolution of HFA 141b is in particular characterized by acidification of the product, but the formation of acid, most particularly of hydrochloric acid, is also accompanied by the formation of other products such as phosgene and peroxide products. It has been possible to demonstrate other decomposition products, in particular formaldehyde, formic acid, glyoxylic acid and monochloroacetic acid. Although the mechanism of this decomposition is not known, it is highly likely that it proceeds via peroxidation of $CV_2$ by ambient or dissolved air and that the various detected products which have been indicated hereinabove are the result of decomposition of the peroxide. It is also impossible to know whether this possible peroxidation of $CV_2$ concerns only the $CV_2$ present in the HFA 141b or whether HFA 141b is not itself susceptible to decomposition into $CV_2$ under the influence of these decomposition products of the same $CV_2$.

This evolution of HFA 141b during storage has been observed in darkness as well as in daylight, but it is much faster in daylight; the phenomenon can be considerably speeded up by irradiation with a UV lamp.

Certain compounds such as nitromethane or nitroethane, which have been widely recommended for stabilization of chlorofluorocarbons and which have been claimed for the stabilization of HFA 141b/methanol mixtures, have absolutely no effect on the stabilization of HFA 141b containing $CV_2$. Neither are phenolic derivatives, in particular hydroquinone monomethyl ether (HQME), very effective.

It has now been found that addition of ethylenic hydrocarbons containing at least 4 carbon atoms to an HFA 141b containing traces of $CV_2$ allows considerable reduction, or even complete inhibition, of this decomposition reaction and that these ethylenic hydrocarbons allow very great stabilization of HFA 141b.

DETAILED DESCRIPTION OF THE INVENTION

The hydrocarbons to be used according to the invention can include one or more ethylenic double bonds and be acyclic (straight-chain or branched) or cyclic (aromatic or non-aromatic) compounds. As non-limiting examples of acyclic ethylenic hydrocarbons, mention may be made of alkenes such as 1- or 2-butene, isobutylene, 1- or 2-pentene, amylene, 2-methyl-1- butene, 1-hexene and diisobutylene, alkadienes such as butadiene, isoprene, 3-methyl-1,2-butadiene and 1,3-pentadiene, and alkatrienes such as alloocimene. As non-limiting examples of cyclic ethylenic hydrocarbons, mention may be made of aromatic compounds such as styrene and α-methylstyrene, and of cycloaliphatic compounds such as dipentene, terpinenes and pinenes.

For certain applications of HFA 141b, it may be advantageous to use as a stabilizer an ethylenic hydrocarbon with a boiling point close to that of HFA 141b (32° C.), and in particular a boiling point between approximately 20° and 45° C.

The quantity of stabilizer required in order to obtain a perfectly stable HFA 141b can vary widely. In general, a quantity of the order of 100 to 1000 ppm of stabilizer is broadly sufficient in order to ensure high stability and preservation of HFA 141b. Such a large quantity is however not always necessary and, in certain cases, contents of a few parts per million (5 to 10 ppm) or of a few tens of ppm (10–100 ppm) are already enough.

Bearing in mind this small quantity of stabilizer, the stabilized product may be used without any drawback instead of a perfectly pure and non-stabilized HFA 141b, in most of its applications.

EXAMPLES

The trials and examples which follow illustrate the invention without limiting it.

TRIAL-A

A sample of 250 g of HFA 141b containing 2000 ppm of 1,1-dichloroethene ($CV_2$) is placed in a pyrex flask and exposed to natural light. At the end of 18 days, the product has become acidic and contains traces of peroxides: 2 mg $H_2O_2$/liter (Merckoquant $R_{10011}$ Peroxide(e) Test indicator paper). After 60 days, the degree of acidity reaches 8 meq. $H+$/kg of HFA 141b.

TRIAL B

A sample of 100 ml of HFA 141b containing 300 ppm of $CV_2$ and 6 ppm of HFA 365 fmc ($CF_3$—$CH_2$—$CF_2$—$CH_3$) is placed in a 25 ml pyrex flask (diameter: 27 mm) and exposed for 5 hours to radiation from a Hanovia 25 W type high-pressure UV lamp (max. wavelength 360 nm), the axis of the flask being situated 26 mm from the edge of the lamp.

At the end of this exposure, the product has become acidic (1.3 meq. $H+$/kg) and gives a positive response to the test for peroxides: 0.5 mg $H_2O_2$/liter. A phosgene assay moreover indicates a content of 13 ppm.

TRIAL C

A sample of 10 ml of the same HFA 141b as for trial B (300 ppm of $CV_2$ and 6 ppm of HFA 365 fmc) is supplemented with 500 ppm of nitromethane, then treated under the same conditions as for trial B. After exposure the product is acidic (3 meq. $H+$/kg) and contains peroxides corresponding to 1 mg $H_2O_2$/liter.

EXAMPLE 1

A sample of 10 ml of the same HFA 141b as for trial B is supplemented with 500 ppm of α-methylstyrene, then exposed as before for 5 hours to radiation from the UV lamp. At the end of the test, HFA 141b reveals no trace of acidity (less than 0.03 meq. $H+$/kg) and no peroxides are detected (content much less than the first measurement level of the test, that is 0.5 mg $H_2O_2$/liter).

EXAMPLE 2

The previous example is repeated with only 200 ppm of α-methylstyrene. No trace of acidity or of peroxide is detected after 5 hours' exposure to radiation from the lamp.

EXAMPLE 3

Example 1 is repeated, the α-methylstyrene being replaced with the same quantity of 1,3-pentadiene (cis and trans mixture). After the test, the product has remained neutral and does not contain peroxides.

EXAMPLES 4 TO 9

Example 1 is repeated, but the α-methylstyrene being replaced with 50 or 100 ppm of 1,3-pentadiene (cis and trans mixture ), 3-methyl-1,2-butadiene or 2-methyl-1-butene. No trace of acidity or of peroxide is detected after 5 hours' exposure to UV radiation.

The table which follows summarizes the preceding trials and examples and their results.

| | STABILIZER | | RESULT | |
|---|---|---|---|---|
| | Nature | Concentration (ppm) | Acidity (meq. $H+$/kg) | Peroxides (mg $H_2O_2$/liter) |
| Trial B | (none) | | 1.3 | 0.5 |
| Trial C | Nitromethane | 500 | 3 | 1 |
| Example 1 | α-methylstyrene | 500 | <0.03 | undetectable (*) |
| Example 2 | α-methylstyrene | 200 | <0.03 | undetectable (*) |
| Example 3 | 1,3-pentadiene | 500 | <0.03 | undetectable (*) |
| Example 4 | 1,3-pentadiene | 100 | <0.03 | undetectable (*) |
| Example 5 | 1,3-pentadiene | 50 | <0.03 | undetectable (*) |
| Example 6 | 3-methyl-1,2-butadiene | 100 | <0.03 | undetectable (*) |
| Example 7 | 3-methyl-1,2-butadiene | 50 | <0.03 | undetectable (*) |
| Example 8 | 2-methyl-1-butene | 100 | <0.03 | undetectable (*) |
| Example 9 | 2-methyl-1-butene | 50 | <0.03 | undetectable (*) |
| Example 10 | 2,-methyl-1,3-butadiene | 100 | <0.03 | undetectable)*) |
| Example 11 | 2-methyl-1,3-butadiene | 50 | <0.03 | undetectable (*) |

(*) very markedly less than 0.5 mg $H_2O_2$/liter.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for stabilization of 1,1-dichloro-1-fluoroethane containing traces of vinylidene chloride, comprising adding a sufficient quantify of at least one acyclic or cycloaliphatic ethylenic hydrocarbon containing at least 4 carbon atoms.

2. Process according to claim 1, wherein the quantity of ethylenic hydrocarbon(s) is between 5 and 1000 ppm in relation to the weight of 1,1-dichloro-1-fluoroethane.

3. Process according to claim 1, wherein the ethylenic hydrocarbon is an alkene.

4. Process according to claim 1, wherein the ethylenic hydrocarbon is an alkadiene.

5. Process according to claim 1, wherein the ethylenic hydrocarbon is a cycloaliphatic compound.

6. Process according to claim 1, wherein the ethylenic hydrocarbon has a boiling point between 20° and 45° C.

7. Process according to claim 6, wherein the ethylenic hydrocarbon is 1,3-pentadiene, 3-methyl-1,2-butadiene, 2-methyl-1-butene, 2-methyl-1,3-butadiene or a mixture of these compounds.

8. 1,1-Dichloro-1-fluoroethane containing 5 to 1000 ppm of at least one ethylenic hydrocarbon as defined in claim 1.

9. Process according to claim 2, wherein the quantity of ethylenic hydrocarbon(s) is between 10 and 100 ppm.

* * * * *